US009156868B2

(12) United States Patent
Zeika et al.

(10) Patent No.: US 9,156,868 B2
(45) Date of Patent: Oct. 13, 2015

(54) ARYL-SUBSTITUTED AND/OR HETEROARYL-SUBSTITUTED MAIN GROUP ELEMENT HALIDES AND/OR PSEUDOHALIDES, USE OF MAIN GROUP ELEMENT HALIDES AND/OR PSEUDOHALIDES, ORGANIC SEMICONDUCTING MATRIX MATERIAL, ELECTRONIC AND OPTOELECTRONIC COMPONENTS

(75) Inventors: Olaf Zeika, New York, NY (US); Michael Limmert, Dresden (DE); Steffen Willmann, Dresden (DE)

(73) Assignee: NOVALED AG, Dresden (DE)

( * ) Notice: Subject to any disclaimer, the term of this patent is extended or adjusted under 35 U.S.C. 154(b) by 939 days.

(21) Appl. No.: 12/596,311

(22) PCT Filed: Apr. 16, 2008

(86) PCT No.: PCT/DE2008/000645
§ 371 (c)(1),
(2), (4) Date: Feb. 5, 2010

(87) PCT Pub. No.: WO2008/128519
PCT Pub. Date: Oct. 30, 2008

(65) Prior Publication Data
US 2010/0140566 A1     Jun. 10, 2010

(30) Foreign Application Priority Data

Apr. 19, 2007   (DE) .......................... 10 2007 018 456

(51) Int. Cl.
| H01B 1/00 | (2006.01) |
| H01B 1/12 | (2006.01) |
| H01L 51/00 | (2006.01) |
| C07F 9/90 | (2006.01) |
| C07F 9/92 | (2006.01) |
| H01L 29/08 | (2006.01) |
| H01L 35/24 | (2006.01) |
| H01L 33/00 | (2010.01) |
| H01B 1/02 | (2006.01) |

(52) U.S. Cl.
CPC . *C07F 9/906* (2013.01); *C07F 9/92* (2013.01); *H01L 51/002* (2013.01); *H01L 51/006* (2013.01); *H01L 51/0078* (2013.01); *Y02E 10/549* (2013.01)

(58) Field of Classification Search
USPC .......... 136/263; 252/500, 519.2; 257/40, 103, 257/E51.047, 607; 313/504; 428/917; 564/426, 434
See application file for complete search history.

(56) References Cited

U.S. PATENT DOCUMENTS

| 2,566,208 | A | * | 8/1951 | Jenkins ......................... 252/572 |
| 3,083,242 | A | | 3/1963 | Ramsden |
| 3,226,450 | A | | 12/1965 | Blazejak et al. |
| 3,367,954 | A | | 2/1968 | Leebrick et al. |
| 3,432,534 | A | | 3/1969 | Remes et al. |
| 3,558,671 | A | | 1/1971 | Martin |
| 3,563,751 | A | | 2/1971 | Cohen |
| 4,003,943 | A | | 1/1977 | Fukunaga |
| 4,066,569 | A | | 1/1978 | Lim |
| 4,133,821 | A | | 1/1979 | West et al. |
| 4,618,453 | A | | 10/1986 | Kim |
| 4,960,916 | A | * | 10/1990 | Pazik ............................. 556/70 |
| 5,093,698 | A | | 3/1992 | Egusa |
| 5,110,835 | A | | 5/1992 | Walter et al. |
| 5,247,226 | A | | 9/1993 | Sato et al. |
| 5,281,730 | A | | 1/1994 | Zambounis et al. |
| 5,292,881 | A | | 3/1994 | Berneth et al. |
| 5,393,614 | A | | 2/1995 | Nakada |
| 5,556,524 | A | | 9/1996 | Albers |
| 5,811,833 | A | | 9/1998 | Thompson |
| 5,840,217 | A | | 11/1998 | Lupo et al. |
| 5,922,396 | A | | 7/1999 | Thompson et al. |
| 6,013,384 | A | | 1/2000 | Kido et al. |
| 6,013,982 | A | | 1/2000 | Thompson et al. |
| 6,103,459 | A | | 8/2000 | Diel et al. |
| 6,207,835 | B1 | | 3/2001 | Reiffenrath et al. |
| 6,350,534 | B1 | | 2/2002 | Boerner et al. |
| 6,423,429 | B2 | | 7/2002 | Kido et al. |
| 6,524,728 | B1 | | 2/2003 | Kijima et al. |
| 6,700,058 | B2 | | 3/2004 | Nelles et al. |
| 6,747,287 | B1 | | 6/2004 | Toguchi et al. |
| 6,824,890 | B2 | | 11/2004 | Bazan et al. |

(Continued)

FOREIGN PATENT DOCUMENTS

| CA | 2549309 | 9/2005 |
| CH | 354065 | 5/1961 |

(Continued)

OTHER PUBLICATIONS

Ouchi, A. et al. Studies of Organometallic Compounds of Group 5B Elements: Synthesis, Infrared and 1H-NMR spectroscopic studies of some carboxylate and phenolato derivatives of triaryl- and trialkylantimony (V) and bismuth (V); Oct. 13, 1975.

(Continued)

*Primary Examiner* — Bijan Ahvazi
(74) *Attorney, Agent, or Firm* — Sutherland Asbill & Brennan LLP

(57) ABSTRACT

The invention relates to aryl- and/or heteroaryl-substituted main group element halides and/or pseudohalides, the use of main group element halides and/or pseudohalides as dopant for the doping of an organic semiconducting matrix material, as charge injection layer, as hole blocker layer, as electrode material, as transport material itself, as memory material in electronic or optoelectronic structural elements.

10 Claims, No Drawings

(56) References Cited

U.S. PATENT DOCUMENTS

| | | | |
|---|---|---|---|
| 6,908,783 B1* | 6/2005 | Kuehl et al. | 438/99 |
| 6,972,334 B1 | 12/2005 | Shibanuma et al. | |
| 7,081,550 B2 | 7/2006 | Hosokawa et al. | |
| 7,345,300 B2 | 3/2008 | Qin | |
| 8,258,501 B2 | 9/2012 | Werner et al. | |
| 2003/0064248 A1 | 4/2003 | Wolk et al. | |
| 2003/0165715 A1 | 9/2003 | Yoon et al. | |
| 2003/0234397 A1 | 12/2003 | Schmid et al. | |
| 2004/0068115 A1 | 4/2004 | Lecloux et al. | |
| 2004/0076853 A1 | 4/2004 | Jarikov et al. | |
| 2005/0040390 A1 | 2/2005 | Pfeiffer et al. | |
| 2005/0061232 A1 | 3/2005 | Werner et al. | |
| 2005/0072971 A1 | 4/2005 | Marrocco et al. | |
| 2005/0086251 A1 | 4/2005 | Hatscher et al. | |
| 2005/0110009 A1 | 5/2005 | Blochwitz-Nimoth et al. | |
| 2005/0121667 A1 | 6/2005 | Kuehl et al. | |
| 2006/0049397 A1 | 3/2006 | Pfeiffer et al. | |
| 2007/0026257 A1 | 2/2007 | Begley et al. | |
| 2007/0058426 A1 | 3/2007 | Sokolik et al. | |
| 2007/0090371 A1 | 4/2007 | Drechsel et al. | |
| 2007/0116984 A1 | 5/2007 | Park et al. | |
| 2007/0145355 A1 | 6/2007 | Werner et al. | |
| 2007/0252140 A1 | 11/2007 | Limmert et al. | |
| 2008/0103315 A1 | 5/2008 | Egawa et al. | |
| 2008/0122345 A1 | 5/2008 | Sakata et al. | |
| 2008/0145708 A1* | 6/2008 | Heil et al. | 428/704 |
| 2008/0265216 A1 | 10/2008 | Hartmann et al. | |
| 2009/0001327 A1 | 1/2009 | Werner et al. | |

FOREIGN PATENT DOCUMENTS

| | | |
|---|---|---|
| CH | 354066 | 5/1961 |
| CN | 1788068 A | 6/2006 |
| DE | 19836408 | 2/2000 |
| DE | 10261662 | 7/2004 |
| DE | 10 2006 053 320 A1 | 5/2008 |
| EP | 1000998 | 5/2000 |
| JP | 61254582 | 11/1986 |
| JP | 63172274 | 7/1988 |
| JP | 63172275 | 7/1988 |
| JP | 04338760 | 11/1992 |
| JP | 7168377 | 7/1995 |
| JP | 2004010703 | 1/2004 |
| JP | 2004335557 | 11/2004 |
| WO | WO 03/088271 | 10/2003 |
| WO | WO 03/104237 | 12/2003 |
| WO | WO 2006/067800 | 6/2006 |
| WO | WO 2008/022633 | 2/2008 |

OTHER PUBLICATIONS

Akiba, Kin-Ya et al., "Direct Synthesis of 2,2-diaryl-3-methyl-2,3-dihydrobenzothiazoles from 3-methyl-2,3-dihydrobenzothiazole-2-thione and some mechanistic aspects," Bulletin of the Chemical Society of Japan, vol. 52(1), pp. 156-159, (1979).

Akutagawa, T. et al. "Multi Electron and Proton-Transfer System Based on 2,2'-biimidazole derivatives," Science and Technology of Syn. Metals, 1994, 346.

Alonso, R. A. et al. "Photostimulated Reaction of Diphenylarsenide and Diphenylstibide Ions with Haloaromatic Compounds by the Srn1 Mechanism. Electron Transfer vs. Bond Breaking of the Radical Anion Intermediate," J. Org. Chem. (1982) 47(1) pp. 77-80.

Auch et al. "Eine neue Synthese und die Kristallstrukturanalyse von., Krokonat-Blau . . . ," Chem. Ber. 120, 1691-1696 (1987), extract, pp. 1691-1693, 6 total pages.

Bach, U. et al. "Solid-state dye-sensitized mesoporous $TiO_2$ solar cells with high photon-to-electron conversion efficiencies," Nature, vol. 395, Oct. 8, 1998, pp. 583-585.

Bamgboye, T.T. et a. "Lewis acidity of $Ph_2SbX_3$, wherein X = Cl or Br. Crystal structures of $Ph_2SbCl_3*H_2O$ and $Ph_2SbBr_3*MeCN$," J. of Organometallic Chem. vol. 362, Feb. 28, 1989, pp. 77-85.

Bard, A. J., Faulkner, R.J., Electrochemical Methods: Fundamentals and Applications, Wiley, 2nd Ed., 2000 (Chapter 6).

Barton, D.H.R. et al. "Comparative Arylation Reactions with Pentaphenylbismuth and with Triphenylbismuth Carbonate," J. Chem. Soc. Chem. Commun. (1980) 17, pp. 827-829.

Baumgartel, H. et al., "Polarographische Untersuchungen zur Konformation von 1.2.3.4.5-pentaarylimidazoliumkationen," Ber. Bunsenges (1972) 76/2, 94-100.

Baumgartel, H. et al.,"Uber eine neue Synthese von tetraaryl-imidazolen und pentaarylimidazolium-salzen," Chem. Ber. (1968), 101, 3504.

Bhattacharya, S.N. et al. "Preparation & Characterization of Some Triarylarsenic & Triarylantimony Mixed Halides & Related Compounds," Indian J. Chem. 16A (1978) pp. 778-781.

Blinka et al. "Octacyanotetramethylenecyclobutane Dianioin and its Anion-Radical," Tetrahedron Lett. (1983). vol. 24, No. 1567-1568.

Blochwitz, J., et al., "Low voltage organic light emitting diodes featuring doped phthalocyanine as hole transport material," Applied Physics Letters, vol. 73, No. 6, Aug. 10, 1998, pp. 729-731.

Bonati, F. et al. "Reactions of C-imidazolyllithium derivatives with Broup Ib compounds: tris[micro-(1-alkylimidazolato-N3, C2)]tri-gold (I) and -silver (I)," J. Organomet. Chem. 1989, 375, pp. 147-160.

Brucsis, L. et al. "Substituionasreaktionen an 1,4-dihalogen-2,3,5,6-tetracyan-benzolen," Chem. Ber. 109(1976) pp. 2469-2474.

Cherkashin M. I. et al. "Studies on 2,4,5-triarylimidazoles," Izv. Akad. Nauk SSSR, Seriya Khim. 1982, 2, pp. 376-377.

Chonan et al. "The synthesis of difluoro and dimethyl derivatives of 2,6-bis(dicyanomethylene)-2,6-dihydro-4H-cyclopenta[2,1-b:3,4-b']-dithiophen-4-one (CPDT-TCNQ) and the Conducting Properties of the Metallic Salts Based on the Dimethy Derivative," The Chemical Society of Japan (2004) pp. 1487-1497.

Curini, M. et al. "Ytterbium Triflate Promoted Synthesis of Benzimidazole Derivatives," Synlett, No. 10, pp. 1832-1834, 2004.

Dedik, S.G. et al. "Tetrahalotetraazafulvalenes—new strong electron acceptors," Chemistry of Heterocyclic Compounds (A Translation of Khimiyageterotsiklicheskikh Soedinenii), Plenum Press Co., New York, U.S., vol. 10, Jan. 1, 1989, p. 1421.

Deluca, Mark et al., "The p-toluenesulfonic acid promoted synthesis of 2-substituted benzoxazoles and benzimidazoles from diacylated precursors," Tetrahedron, vol. 53, No. 2, pp. 457-464, 1997.

Endo, Jun et al., "Organic Electroluminescent Devices with a vacuum-deposited Lewis Acid doped hole injecting layer," Japan Society of Applied Physics, vol. 41, 2002, pp. L358-L360, Part 2, No. 3B, Mar. 15, 2002.

Fatiadi et al. "Electrochemical Oxidation of Several Oxocarbon Salts in N,N-dimethylformamide," J. Electroanalytical Chem. (1982) vol. 135, pp. 193-209.

Fatiadi, "Psuedooxocarbons, Synthesis of 1,2,3-tris(dicyanomethylene)croconate Salts; A New Bond-Delocalized Dianion, Croconate Blue," J. Org. Chem. 1980, 45, 1338-1339.

Fatiadi, "Synthesis of 1,3-(dicyanomethylene)croconate Salts. New Bond-Delocalized Dianion, Croconate Violet," Journal of the American Chemical Society, Apr. 12, 1978, pp. 2586-2587.

Fausett, B.W. et al. "Palladium-catalyzed coupling of thiol esters with aryl and primary and secondary alkyl organiindium reagents," J. Org. Chem. (2005) 70(12) pp. 4851-4853.

Fenghong Li et al., "Leuco Crystal Violet as a dopant for n-doping of organic thin films of fullerene C60," J. Phys. Chem. B 2004, 108, pp. 17076-17088.

Fild, Manfred et al. "Group VA pentafluorophenyl compounds. 14. Pentafluorophenyl-substituted phosphoranes," Zeitschrift Fuer Anorganische und Allgemeine Chemie, 439, pp. 145-152 (1978).

Fukunaga, T. et al. "Negatively substituted trimethylenecyclopropane dianions," J. Am. Chem. Soc., 1976, pp. 610-613.

Gan, F. "Optical nonlinearity of hybrid and nanocomposite materials prepared by the Sol-Gel method," J. of Sol-Gel Science and Technology, 13, 559-563 (1998).

Ganzorig, C. et al., "p-Typed Semiconducts of Aromatic Diamines Doped with $SbCl_5$," Chemistry Letters 2000, pp. 1032-1033.

Gibbons, M.N. et al. "Multiply Bridged Diantimony Compounds," Phosphorus, Sulfur, & Silicon 93/94 (1994).

Giovanella, et al. "Electroluminescence from two fluorinated organic emitters embedded in polyvinyl carbazole," Applied Physics Letters, vol. 87, pp. 171910-1-3.

(56) References Cited

OTHER PUBLICATIONS

Glemser, O. et al. "Synthese von Tris-pentafluorphenylarsin, -stibin und -phosphin sowie von Trimethyl-pentafluor-phenylsilan," Angew. Chemie (1964) 76, 953.

Gogoi, P. et al. "An efficient and one-pot synthesis of imidazolines and benzimidazoles via anaerobic oxidation of carbon-nitrogen bonds in water," Tetrahedron Lett. 2006, 47, pp. 79-82.

Gregg, B.A. et al., "On the superlinear increase in conductivity with dopant concentration in excitonic semiconductors," Applied Physics Letters, vol. 84, No. 10, Mar. 8, 2004, pp. 1707-1709.

Grimmett, M. R., "Imidazole and benzimidazole synthesis," Tables of Contents, pp. 1-10, Academic Press, Harcourt Brace & Company, Publishers, London, San Diego, NY, Boston et al., 1997.

Gufeng, HE et al., "High-efficiency and low-voltage p-i-n electrophosphorescent organic light-emitting diodes with double-emission layers," Applied Physics Letters, vol. 85, No. 17, Oct. 25, 2004, pp. 3911-3913.

Haddon, R.C. et al., "Conducting films of C60 and C70 by alkali-metal doping," Nature, vol. 350, Mar. 28, 1991, pp. 320-322.

Harada, Kentaro et al., "Realization of organic pn-homojunction using a novel n-type doping technique, Proceedings of SPIE—The international Society for Optical Engineering; Organic Optoelectronics and Photonics 2004," vol. 5464, Sep. 2004, pp. 1-9.

Harris, G. S. et al."The Reaction of Trispentafluorophenylstibine with Halogens and Interhalogens," J. Fluorine Chem. 37 (1987) pp. 247-252.

Heinze, J. et al., "Polarographic studies of the conformation of 1,2,3,4,5-pentaarylimidazolium cations," The Institute for Physical Chemistry at the University of Freiburg, pp. 1-22, 1972.

Hill, J. "Oxidative Dimerization of Benzimidazole," J. Org. Chem. 1963, 28, pp. 1931-1932.

Hopf et al. "Uber einen neuen Kohlenwasserstoff C18H24 . . . ," Helvetica Chimica Acta, vol. XLIV, Issue II (1961), No. 46, extract from p. 380-386.

Hopf et al., "Preparation and Properties, Reactions, and Applications of Radialenes," Angewandte Chemie, vol. 31, No. 8, Aug. 1992, pp. 931-954.

Iyoda, et al. "Novel synthesis of hexaaryl[3]radialenes via dibromo[3]dendralenes," Tetrahedron Letters 41 (2000), 6 pgs.

Japp, F. et al. "Constitution of Glycosine," J. Chem. Soc. Trans. 1887, 51, pp. 552-557.

Jefferson, Alan M. and Suschitzky, H., "New Route to Nucleophillically Substituted o-phenylenediamines," J.C.S. Chem. Comm. pp. 189-190, 1997.

Jensen, W.B.; The Generalized Lewis Acid Based Concepts, John Wiley & Sons, New York, 1980, pp. 113-195.

Ji, L. et al. "Mono-, di- and tetra-nuclear ruthenium (II) complexes containing 2,2'-p-phenylenebis(imidazo[4,5-f]phenanthroline): synthesis, characterization and third-order non-linear optical properties," J. Chem. Soc., Dalton Trans. 2001, pp. 1920-1926.

Katz, H.E. et al. "Pyridyl Dicyanoquinodimethane Acceptors for Electroactive Solids," J. Org. Chem. 56 (1991) pp. 5318-5324.

Kaufhold, Von Jurgen et al., "Uber das Leitfahigkeitsverhalten verschiedener Phthalocyanine im Vakuum und unter dem Einfluss von gasen," Ber. Bunsen. Phys. Chem. 69, pp. 168-179.

Kikuchi, A et al. "A new family of pi-conjugated delocalized biradicals: electronic structures of 1,4-bis(2,5-diphenylimidazol-4-ylidene)cyclohexa-2,5-diene," J. Phys. Chem. B., 2005, 109, pp. 19448-19453.

Kikuchi, A. et al. "Definitive Evidence for the Contribution of Biradical Character in a Closed-Shell Molecule, Derivative of 1,4-Bis-(4,5-diphenylimidazol-2-ylidene)cyclohexa-2,5-diene," J. Am. Chem. Soc. 2004, 126, pp. 6526-6527.

Kimura, M. et al. "Preparation of 4-(4,5-diphenyl-1H-imidazol-2-yl)benzaldehyde and its Practical Synthetic Use in the Synthesis of Unsymmetrically Substituted Imidazoles," ITE Letters on Batteries, New Technologies and Medicine, 2002, 3, pp. 30-34.

Klopman, G. "Chemical Reactivity and the Concept of Charge-and Frontier-controlled reactions," Journal of the American Chemical Society., vol. 90, No. 2, Jan. 17, 1968, pp. 223-234.

Koster, et al. "Synthesis and reactions of a tetraquinocyclobutane," Dept. of Chemistry, Univ. of Wisconsin, J. Org. Chem., vol. 40, No. 16, 1975, pp. 2300-2304.

Kozaki, M. et al. "Preparation, Properties, and Reduction of Heteroaromatic Quinoids with 1,4-diazacyclopentadien-2-ylidene Terminals," Org. Lett. 2005, 7, pp. 115-118.

Krebs, F.C. et al. "Superradiant properties of 4,4'-bis(1H-phenanthro[9,10-d]imidazol-2-yl)biphenyl and how a laser dye with exceptional stability can be obtained in only one synthetic step," Tetrahedron Lett. 2001, 42, pp. 6753-6757.

Kulkarni, A.P. et al., "Electron transport materials for organic light-emitting diodes," Chem. Mater. 2004, 16, pp. 4556-4573.

Lane, E.S. "A Modified Benziminazole Synthesis," J. Chem. Soc. 1953, pp. 2238-2240.

Lehmstaedt, K. et al. "Halogen-2,2'-diimidazole und ihre Umsetzungen mit Aminen zu Farbstoffen," Ber. Dt. Chem. Ges. B, 1943, pp. 879-891.

Leyden, R. et al. "Thermally Induced Degradation of 2,3,5,6-tetrachloroterephthalylidenebis(o-aminoaniline)," J. Org. Chem. 1983, 48, pp. 727-731.

Li, J. Y. et al. "Enhancement of green electroluminescence from 2,5-di-p-anisyl-isobenzofuran by double-layer doping strategy," Preparation and Characterization, vol. 446, No. 1, pp. 111-116.

Ludvik, J. and Pragst, F. et al., "Electrochemical generation of triplet states," Journal of Electroanalytical Chemistry, No. 180, pp. 141-156, (1984).

Ludvik, J. and Volke, J. "Evidence for a radical intermediate in the anodic oxidation of reduced nicotinamide adenine dinucleotides obtained by electrogenerated chemiluminescence," Analytica Chimica Acta, 209 (1988) 69-78.

Maennig, B. et al., "Organic p-i-n solar cells," App. Phys. 2004, A 79, pp. 1-14.

Matschke, M. et al. "Bis-4h-imidazoles-tetraazafulvalenes-2,2'-biimidazoles: three variations of one redox system," Tetrahedron, vol. 62, No. 36, Sep. 4, 2006, pp. 8586-8590.

Mayer, U. et al. "Uber 2,3,6,7-tetraphenyl-1,4,5,8-tetraazafulvalen," Tetrahedron Lett. 1966, 42, pp. 5221-5223.

Mayer, U. et al. "Uber Biradikale, Chinone und Semichinone der Imidazolyl-Reihe," Angew. Chem. 1966, 78, p. 303.

Minoura, M. et al. "Hexaaryltellurium, the First Neutral Compounds Comprising Hexaarylated Elements," Angew. Chem. Int. Edit. 35 (22) pp. 2660-2662 (1996).

Miyasato, M. et al. "Syntheses and Reactions of Hexavalent Organitellurium Compounds Bearing Five or Six Tellurium—Carbon Bonds," Chem.—A European J. 10(10) pp. 2590-2600 (2004).

Muramatsu, T. et al, "Visible Light Sensitive Cyclomer and its Tautomeric Dispiro Compound Formed from Bispyridiny Diradical," J. Am. Chem. Soc. 2005, 127, 4572-3.

Muramatsu, T. et al., "Photosensitive Cyclomer Formation of 1,1'-(1,2-ethanediyhbis(pyridinyl) diradical and its derivativese," J. Am. Chem. Soc. 1989, 111, 5782-7.

Muramatsu, T. et al., "Preparation and Properties of a novel heterocyclic dispiro compound, 3, 10-diaza-N,N-dimethyldispiro[5.0.5.3]pentadeca-1,4,8,11-tetraene," Chemistry Letters, pp. 151-152, (1996).

Nelsen, Stephen, F.; "Heterocyclic Radical Anions. II. Naphthalic and 1,4,5,8-Naphthalenetetracarboxylic Acid Derivatives," Journal of the American Chemical Society, 89:23, Nov. 8, 1967, pp. 5925-5931.

Oeter, D. et al., "Doping and Stability of Ultrapure alpha-oligothiophene Thin Films," Synthetic Metals, 61, 1993, pp. 147-150.

Okada, K. et al. "Detection of a diradical intermediate in the cis-trans isomerization of 5,5'- bis(4,5-diphenyl-2H-imidazol-2-ylidene)-5,5'-dihydro-delta 2,2'-bithiophene," Tetrahedron Lett. 2006, 47, pp. 5375-5378.

Okada, K. et al. "Novel Dimers of 2,2'-(m-Phenylene)bis(4,5-diphenyl-1-imidazolyl) Diradical," Chem. Lett. 1998, pp. 891-892.

Otero, A. et a. "Pentachlorophenyl-arsenic, -antimony and -bismuth compounds," J. of Organometallic Chemistry, vol. 171, No. 3, Jan. 1, 1979, pp. 333-336.

Otero, A. et al. "Pentafluorophenylantimony compounds," J. Organometallic Chem. 154 (1978) pp. 13-19.

(56) References Cited

OTHER PUBLICATIONS

Ouchi, A. et al. "13C-nuclear magnetic resonance of some triaryl- and tri-alkylantimony and -bismuth derivatives," J. of Inorganic and Nuclear Chemistry, vol. 37, Issue 11, Nov. 1975, pp. 2347-2349.

Ouchi, A. et al. "The syntheses and properties of some alkylthioacetato and arylthioacetato derivatives of triphenylantimony(V) and -bismus (V)," J. of Inorganic and Nuclear Chemistry, vol. 37, Issue 12, Dec. 1975, pp. 2559-2561.

Park, S. B. et al. "Highly Efficient, Recyclable Pd(II) Catalysts with Bisimidazole Ligands for the Heck Reaction in Ionic Liquids," Organic Lett. 2003, 5, pp. 3209-3212.

Parthasarathy, G. et al., "Lithium doping of semiconducting organic charge transport materials," J. Appl. Phys., vol. 89, No. 9, May 1, 2001, pp. 4986-4992.

Petzhold, C. "Beitrage zur Synthese funktioneller 1,4,5,8-tetraazafulvalene," Dissertation; Friedrich-Schiller-Universitat Jena; 2006.

Pfeiffer, M, et al., "Doped Organic semiconductors: physics and application in light emitting diodes," Organic Electronics, Elsevier, Amsterdam, NL, vol. 4, No. 2/3, Sep. 2003, pp. 89-103, XP001177135, ISSN: 1556-1199.

Quast, H. and Schmitt, E.; "Note Regarding the Quaternization of Heterocycles," Institute of Organic Chemistry at the University of Wurzburg, Chem. Ber. 101, pp. 4012-4014, (1968).

Rake, A. T. et al. "Pentafluorophenyl and phenyl-phosphinidene ions and their group V analogues," Oms. Organic Mass Spectrometry, vol. 3 Jan. 1, 1970, pp. 237-238.

Rasmussen, P.G. et al. "Complexes of the New Ligand Tetracyanobiimidazole," J. Am. Chem. Soc. 1982, 104, pp. 6155-6156.

Rezende, M. C. et al. "An Alternative Preparation of Bisbenzimidazoles," Syn. Comm. 2001, 31, pp. 607-613.

Rezende, M. et al. "Puzzling Formation of Bisimidazole Derivatives from Hexachloroacetone and Diamines," Tetrahedron Lett. 1996, 37, 5265-5268.

Sakaino, Y. "Structures and Chromotropic Properties of 1,4-bis(4,5-diphenylimidazol-2-yl)benzene Derivatives," J. Org. Chem. 1979, 44, pp. 1241-1244.

Sato, S. et al. "Isolation and Molecular Structure of the Organopersulfuranes [12-S-6(C6)]," J. Am. Chem. Soc. 128(21) pp. 6778-6779 (2006).

Schmidt, "Reaktionen von Quadratsaure und Quadratsaure-Derivaten," Synthesis, Dec. 1980, extract pp. 966, 24 total pages.

Schneiders, P. et al. "Notiz zur Darstellung von 4,4',5,5'-tetrasubstituierten Di-2-imidazolyl-derivaten. Ausgangsprodukte zur Darstellung von 1,4,5,8-tetraazafulvalenen," Chem. Ber. 1973, 106, pp. 2415-2417.

Schwarz, W. M. et al., "Formation of Stable Free Radicals on Electroreduction of N-alkylpyridium salts," J. Am. Chem. Soc., 33 3164 (1961).

Seitz, G., Nachr. Chem. Tech. Lab 28 (1980), No. 11, extract pp. 804-807, total pp. 6: "Pseudooxokohlenstoffe."

Sekine, T. et al. "Dimerizations of pi-Rich N-heteroaromatic compounds and xanthine derivatives," Chem. Pharm. Bull. 1989, 37, pp. 1987-1989.

Sharma, G.D. et al., "Influence of Iodine on the Electrical and Photoelectrical Properties of Zinc Phthalocyanine Think Film Devices," Materials Science and Engineering, B41, 1996, pp. 222-227.

Singhal, K. et al. "One the Lewis acidity of tris(pentafluorophenyl)antimony (V) dichloride towards neutral monodentate O, N and S donor ligands," Journal of Fluorine Chemistry, vol. 121, No. 2, Jun. 1, 2003, pp. 131-134.

Smith, M.B. Organic Synthesis, McGraw-Hill, Inc. 1994, Chapter 1.

Sprenger, et al. "The cyclobutenediylium cation, a novel chromophore from squaric acid," Angew. Chem. International Edition, vol. 6 (1967), No. 6, pp. 553-554.

Suschitzky, H. "Syntheses and Reactions of 2,2'-bisbenzimidazole Systems," J. Heterocyclic Chem. 1999, 36, pp. 1001-1012.

Suzuki, T. et al., "4,7-bis(dimethylamino)benzimidazoles and twin-type derivatives: reversible two-stage redox system modulated by proton-transfer," Tetrahedron Lett. 2003, 44, pp. 7881-7884.

Takahashi et al. "Novel Electron Acceptors for Organic Condcutors: 1,2-Bis(p-benzoquino)-3-[2-(dicyanomethylene)-2,5-thienoquino]cyclopropane Derivatives," J. Chem. Soc., Chem. Commun., 1994, pp. 519-520.

Takahashi et al. "Novel metallic charge-transfer complexes composed of a [3]radialene type acceptor: a 1,2-bis(p-benzoquino)-3-[2-(dicyanomethylene) . . . " Advanced Materials, July, No. 7, 3 pgs.

Vaid T.P. et al, "Investigations of the 9,10-diphenylacridyl radical as an isostructural dopant for the molecular semiconductor 9, 10-diphenylanthracene," Chemistry of Materials, American Chemical Society, Bd. 15, Nr. 22, 4292-4299 (2003).

Vyas, P.C. et al. "A simple synthesis of 2,2'-bis-benzimidazoles," Chem. Industry, 1980, pp. 287-288.

Weiss, M. "Acetic Acid-Ammonium Acetate Reactions. 2-Isoimidazoles as Intermediates in Imidazole Formation," J. Am. Chem. Soc. 1952, 74, pp. 5193-5195.

West, R. et al., "Diquinocyclopropanones, Diquinoethylenes, and the Anion-Radical and Free-Radical Intermediates in their Formation," Dept. of Chemistry, Univ. of Wisconsin, Feb. 24, 1975, pp. 2295-2299.

Wintgens, V. et al., "Reduction of Pyrylium Salts: Study by ESR and UV_Visible Spectroscopy of the Reversible Dimerization of the Pyranyl Radical," New. J. Chem., 10/6, 345-350 (1986).

Yamaguchi, et al., "New Approaches to Tetracyanoquinodimethane," Bull. Chem. Soc. Jpn. 62 (1989) pp. 3036-3037.

Yamamoto, Y. et al. "The Electrical Properties of the Poly(N-vinyl Carbazole)-Antimony (V) Chloride (or Iodine) Charge Transfer Complexes," Bull. Chem. Soc. Jap. 1965, 38, 2015-2017.

Yoshiko, S., et al. "The Quinoid-biradical Tautomerism of 3,6-bis(4,5-diphenyl-2H-imidazol-2-ylidene)-1,4-cyclohexadiene," Nippon Kagaku Kaishi, 1972, 1, pp. 100-103.

Yukihiko, T., et al. "Studies on Aromatic Nitro Compounds. V. A Simple One-Pot Preparation of o-Aminoaroylnitriles from Some Aromatic Nitro Compounds," Chem. Pharm. Bull., 33 (4) 1360-1366 (1985).

Zhou, X et al., "Enhanced hole Injection Into Amorphous Hole-Transport Layers of Organic Light-Emitting Diodes Using Controlled p-Type Doping," Adv. Funct. Mater., 2001, 11, No. 4, pp. 310-314.

Ziegenbein, W. "The cyclobutenediylium cation, a novel chromophore from squaric acid," Angew. Chem., 79:12, pp. 581-582 (1967).

English Translation of Japanese Office Action; Japanese Patent Application No. 2005-228491; Apr. 17, 2009.

International Search Report, International App. No. PCT/EP2007/002359, May 24, 2007.

Final Office Action, U.S. Appl. No. 11/688,777; Nov. 27, 2009.

Non-Final Office Action, U.S. Appl. No. 11/688,777; Feb. 2, 2009.

Response to Office Action, U.S. Appl. No. 11/688,777; Sep. 4, 2009.

Response to Office Action, U.S. Appl. No. 11/688,777; Aug. 3, 2009.

Restriction Requirement, U.S. Appl. No. 11/688,777; Mar. 5, 2010.

Response to Restriction Requirement, U.S. Appl. No. 11/688,777; Apr. 1, 2010.

Notice of Allowance, U.S. Appl. No. 11/196,491; Apr. 13, 2009.

Notice of Allowance, U.S. Appl. No. 11/196,491; Oct. 20, 2008.

Response to Office Action for U.S. Appl. No. 11/196,491; Aug. 11, 2008.

Final Office Action, U.S. Appl. No. 11/196,491; Feb. 11, 2008.

Response to Office Action for U.S. Appl. No. 11/196,491; Nov. 5, 2008.

Non-Final Office Action, U.S. Appl. No. 11/196,491, Jul. 3, 2007.

International Search Report and Preliminary Report on Patentability for PCT/DE2008/001080; Jul. 11, 2008.

International Search Report for PCT/DE2008/00654; Jun. 15, 2009.

International Search Report and Preliminary Report on Patentability for PCT/EP2006/010816; Feb. 9, 2007.

Advisory Action for U.S. Appl. No. 11/315,072 mailed Mar. 8, 2010.

Response to Final Office Action for U.S. Appl. No. 11/315,072; Feb. 17, 2010.

Final Rejection for U.S. Appl. No. 11/315,072; Nov. 16, 2009.

(56) References Cited

OTHER PUBLICATIONS

Response to Office Action for U.S. Appl. No. 11/315,072; Jul. 29, 2009.
Non-Final Rejection for U.S. Appl. No. 11/315,072; Apr. 29, 2009.
Non-Final Rejection for U.S. Appl. No. 11/315,072; Nov. 12, 2008.
Response to Office Action for U.S. Appl. No. 11/315,072; Feb. 10, 2009.
European Search Report for EP 07009366; Oct. 19, 2007.
International Search Report for PCT/EP2008/003792; Sep. 2, 2008.
Anderson, J.D. et al., "Electrochemistry and Electrogenerated Chemiluminescence Processes of the Componenets of Aluminum Quinolate/Triarylamine, and Related Organic Light emitting Diodes," J. Am. Chem. Soc., 1998, 120, pp. 9646-9655.
Bard, A. J., Faulkner, R.J., Electrochemical Methods: Fundamentals and Applications, Wiley, 2nd Ed., 2000 (Chapter 2).
D'Andrade, B.W. et al., "Relationship between the ionization and oxidation potentials of molecular organic semiconductors," Organic Electronics 6, 2005, pp. 11-20.
Harada, K. et al. "Organic Homojunction Diodes with a High Built-in Potential: Interpretation of the Current-Voltage Characteristics by a Generalized Einstein Relation," Phys. Rev. Lett. 94, 036601 (2005).
Huang, Jingsong et al., "Low-voltage organic electroluminescent devices using pin structures," Applied Physics Letters, vol. 80, No. 1, Jan. 7, 2002, pp. 139-141.
Maitrot, M. et al., "Molecular material based junctions: Formation of a Schottky Contact with Metallophthalocyanine Thin Films Doped by the Cosublimation Method," J. Applied Physics, 60(7), Oct. 1, 1986, pp. 2396-2400.
Miller, L.L. et al., "A simple comprehensive correlation of organic oxidation and ionization potentials," J. Org. Chem., 1972, vol. 37, No. 6, pp. 916-918.
Nollau, A. et al., "Controlled n-type doping of a molecular organic semiconductor: naphthalenetetracarboxylic dianhydride (NTCDA) doped with bis(ethylenedithio)-tetrathiafulvalene (BEDT-TTF)," J. Appl. Phys., vol. 87, No. 9, May 1, 2006, pp. 4340-4343.
Parker, "On the Problem of Assigning Values to Energy Changes of Electrode Reactions," Journal of the American Chemical Society, 96:17, Aug. 21, 1974, pp. 5656-5661.
Pfeiffer, M. et al., "Controlled doping of phthalocyanine layers by cosublimation with acceptor molecules: A systematic Seebeck and conductivity study," Applied Physics Letters, vol. 73, No. 22 Nov. 20, 1998, pp. 3202-3204.
R. Schlaf et al., "Homo/Lumo Alignment at PTCDA/ZnPc and PTCDA/ClInPc Heterointerfaces Determined by Combined UPS and XPS Measurements," J. Phys. Chem. B 1999, 103, pp. 2984-2992.
Tang, C.W. et al., "Organic electroluminescent diodes," Applied Physics Letters, vol. 51, No. 12, Sep. 21, 1987, pp. 913-915.
Tang, T.B. et al., "Ionization thresholds of merocyanine dyes in the solid state," Journal of Applied Physics, vol. 59, (1), Jan. 1986, pp. 5-10.
Werner, A. G. et al., "Pyronin B as a donor for n-type doping of organic thin films," Applied Physics Letters, vol. 82, No. 25, Jun. 23, 2003, pp. 4495-4497.
Yao, Fu et al., "Quantum-chemical predictions of Absolute standard redox potentials of diverse organic molecules and free radicals in acetonitrile," J. Am. Chem. Soc. 2005, 127, pp. 7227-7234.
Zhou, X. et al., "Very low operating voltage organic light-emitting diodes using a p-doped amorphous hole injection layer," Applied Physics Letters, vol. 78, No. 4, Jan. 22, 2001, pp. 410-412.
Zimmerman, T. et al. "Benzocycloalkenone und dihydro-2H, 7H-1-benzopyranone aus 2,4,6-triaryl-pyryliumsalzen und cycloalkan-1,2-dionen," J. Prakt. Chem. 331 pp. 306-318 (1989).
Non-Final Rejection for U.S. Appl. No. 12/046,620; Nov. 25, 2009.
Response to Restriction Requirement for U.S. Appl. No. 12/046,620; Aug. 24, 2009.
Restriction Requirement for U.S. Appl. No. 12/046,620; Jul. 22, 2009.
Disclosure Under 37 C.F.R. § 1.56 for U.S. Appl. No. 12/593,311 Submitted Herewith.
Gao, W. et al., "Effect of electrical doping on molecular level alignment at organic-organic heterojunctions," Applied Physics Letters, vol. 82, No. 26, Jun. 30, 2003, pp. 4815-4817.
Kido, Junji et al., "Bright Organic Electroluminescent Devices Having a Metal-doped Electron-injecting Layer," Applied Physics Letters, vol. 73, No. 20, Nov. 16, 1998, pp. 2866-2868.
Examination Notification in counterpart Taiwan Patent Application No. 097113705 mailed Jan. 7, 2013 (English translation).
"On the Lewis acidity of tris(pentafluorophenyl)antimony(V) dichloride towards neutral monodentate O, N and S donor ligands," Journal of Fluorine Chemistry (2003), 121(2), 131-134, abstract, CAPLUS.
"Silver compounds in synthetic chemistry," Journal of Fluorine Chemistry (2006)127(2), 213-217, abstract, CAPLUS.
"Perfluoroaryl substituent effects in metallocene-catalyzed olefin polymerization," Abstracts of Papers, 220th ACS National Meeting, 2000.
Raj et al., "The Preparation of Pentafluorophenyl Antimony (III) and Antimony (V) Halides and Mixed Halides," Journal of Fluorine Chemistry, 1989, 42:163-172.
Taiwanese Office Action for TW Application No. 097113705 mailed Aug. 16, 2013 (8 pages) (English translation).

* cited by examiner

ARYL-SUBSTITUTED AND/OR HETEROARYL-SUBSTITUTED MAIN GROUP ELEMENT HALIDES AND/OR PSEUDOHALIDES, USE OF MAIN GROUP ELEMENT HALIDES AND/OR PSEUDOHALIDES, ORGANIC SEMICONDUCTING MATRIX MATERIAL, ELECTRONIC AND OPTOELECTRONIC COMPONENTS

CROSS-REFERENCE TO RELATED APPLICATION

This is a submission pursuant to 35 U.S.C. 154(d)(4) to enter the national stage under 35 U.S.C. 371 for PCT/DE2008/000645 filed Apr. 16, 2008. Priority is claimed under 35 U.S.C. 119(a) and 35 U.S.C. 365(b) to German Patent Application Number 10 2007 018 456.7 filed Apr. 19, 2007. The subject matters of PCT/DE2008/000645 and German Patent Application Number 10 2007 018 456.7 are hereby expressly incorporated herein by reference in their entirety.

The invention relates to aryl- and/or heteroaryl-substituted main group element halides and/or pseudohalides, the use of main group element halides and/or pseudohalides as dopant for the doping of an organic semiconducting matrix material, as charge injection layer, as hole blocker layer, as electrode material, as transport material itself, as memory material in electronic or optoelectronic structural elements as well as to an organic semiconducting material and electronic or optoelectronic structural elements.

The changing of organic semiconductors by doping as regards their electrical properties, especially their electrical conductivity, as is also the case for inorganic semiconductors such as silicon semiconductors, is known. This achieves an elevation of the conductivity, which is quite low at first, as well as, depending of the type of dopant used, a change in the Fermi level of the semiconductor by generating charge carriers in the matrix material. A doping results here in an elevation of the conductivity of charge transport layers, as a result of which ohmic losses are reduced, and in an improved transition of the charge carriers between contacts and organic layer. Inorganic dopants such as alkali metals (e.g., cesium) or Lewis acids (e.g., $FeCl_3$, $SbCl_5$) are usually disadvantageous for organic matrix materials on account of their high coefficients of diffusion since the junction and stability of the electronic structural elements is adversely affected, see D. Deter, Ch. Ziegler, W. Göpel Synthetic Metals (1993) 61 147-50; Y. Yamamoto et al. (1965) 2015, J. Kido et al. Jpn J. Appl. Phys. 41 (2002) L358-60. Moreover, the latter dopants have such a high vapor pressure that a technical use is very questionable. In addition, the reduction potentials of these compounds are often too low for doping technically really interesting hole conductor materials. In addition, the extremely aggressive reaction behavior of these dopants makes a technical application difficult.

The present invention is based on the object of making compounds available that can be used as dopant, as charge injection layer, as hole blocker layer, as electrode material, as transport material itself or as memory material. The compounds should preferably have sufficiently high reduction potentials, be without disturbing influences on the matrix material and make available an effective elevation of the charge carrier number in a matrix material and be able to be relatively simply handled.

Further tasks of the present invention consist in the usage of corresponding compounds as dopant for doping an organic semiconducting matrix material, as charge injection layer, as electrode material, as transport material itself as well as memory material in electronic or optoelectronic structural elements, as well as in the making available of organic semiconducting materials and of electronic structural elements or optoelectronic structural elements in which the disclosed compounds can be used.

The first object is solved by aryl- and/or heteroaryl-substituted main group element halides and/or pseudohalides, characterized by the following structure: $R_n$-M-$X_m$, wherein M is a main group element, R is independently selected from non-substituted and electron-acceptor-substituted aryl, heteroaryl, preferably electron-poor heteroaryl, and —Z-M$R_n X_m$, wherein Z is selected from O, S, alkylene, $NR_1$ with $R_1$=CN, halogen, alkyl, heteroalkyl or aryl, O—$(R_2)_x$—O with $R_2$=alkyl or aryl and with x=1-6, wherein X is independently selected from halogen and pseudohalogen, n=1-6 and m=1, 2, 3, 4, or 5, or wherein the groups R are connected to each other at least in pairs, directly or via a bridge, preferably via O, S or alkylene, with the following compounds being excluded: (1,4-Dihydro-1-phenyl-5H-tetrazole-5-thionato-N4)bis(pentafluorophenyl)SbNCSCl; Bis(pentafluorophenyl)(4-tolyl)antimony (V)dichloride; Hexa(4-trifluoromethylphenyl)tellurium(VI); Penta(4-trifluoromethylphenyl)tellurium(VI)chloride; Penta(4-trifluoromethylphenyl)tellurium(VI) bromide; Bis([1,1'-biphenyl]-2,2'-diyl)seleniumdifluoride; Bis([1,1'-biphenyl]-2,2'-diyl)telluriumdi-fluoride; Bis([1,1'-biphenyl]-2,2'-diyl)telluriumdichloride; Tetraphenyltellurium(VI)difluoride; Tri(pentafluorophenyl)tellurium(IV)halide; Tri(pentafluorophenyl)tin(IV)halide; Tri(penta-fluorophenyl)germanium (IV)halide; Tri(pentafluorophenyl)silicon(IV)halide; Bis(pentafluorophenyl)germanium(IV)dihalide; Bis(pentafluorophenyl)tellurium(IV)dihalide; Bis(pentafluorophenyl)M(IV)dihalide with M=Si, Se, S; Bis(pentafluorophenyl)tin(IV)dichloride; Bis(pentafluorophenyl)tin(IV)dibromide.

It should be noted regarding the structure of the main group element halides and/or pseudohalides shown in the claims that these compounds have at least one group ft, so that n≥1.

In accordance with the valence of the main group elements. e.g., the following substructures can fall under the structure shown in the claims:

If the central atom M is, e.g., S, Se or Te, then a structure $R_{1-6}$-M-$X_{0-5}$ can result. If the central atom M is, e.g., P, As, Sb or Bi, a structure $R_{1-5}$-M-$X_{0-4}$ can result. If the central atom M is, e.g., Al, Ga, In, Tl, P, As, Sb or Bi, a substructure $R_{1-3}$-M-$X_{0-2}$ results. If the central atom M is, e.g., Si, Sn, S, Se, Te or Pb, a substructure $R_{1-4}$-M-$X_{0-3}$ results.

These aryl- and/or heteroaryl-substituted main group element halides and/or pseudohalides can also be used as hole injection layer. Thus, e.g., a layer structure anode/acceptor/hole transporter can be produced. The hole transporter can be a pure layer or a mixed layer. In particular, the hole transporter can also be doped with an acceptor. The anode can be, e.g., ITO. The acceptor layer can be, e.g., 0.5-100 nm thick.

It was surprisingly determined that given a use in accordance with the invention of the disclosed main group element halides and/or pseudohalides a significantly stronger and/or more stable dopant is present than in the case of previously known acceptor compounds, wherein the main group element halides and/or pseudohalides are used in neutral form as p-dopant in an organic semiconducting matrix material. What was stated above applies in particular to aryl- and/or heteroaryl-substituted main group element halides and/or pseudohalides. In particular, the conductivity of charge carrier transport layers is significantly increased in the usage in accordance with the invention and/or the transition of the charge carriers between the contacts and organic layer is significantly improved in applications as electronic structural element. Without being limited to this concept, it is assumed that in the usage of the main group element halides and/or pseudohalides in accordance with the invention in a doped layer CT complexes are formed, in particular by the transfer of at least one electron of the particular surrounding matrix material. Likewise, cations of the matrix material are formed that can move on the matrix material. In this manner the matrix material gains a conductivity that is elevated in contrast to the conductivity of the non-doped matrix material. Conductivities of non-doped matrix materials are as a rule $<10^{-8}$ s/cm, especially frequently $<10^{-10}$ s/cm. Care is to be taken here that the matrix material has a sufficiently high purity. Such purities can be achieved with traditional methods, e.g., gradient sublimation. The conductivity of such matrix materials can be increased by doping to greater than $10^{-8}$ s/cm, frequently $>10^{-5}$ s/cm. This applies in particular to matrix materials that have an oxidation potential greater than $-0.5$ V vs. Fc/Fc$^+$, preferably greater than 0 V vs. Fc/Fc$^+$, especially greater than $+0.2$ V vs. Fc/Fc$^+$. The indication Fc/Fc$^+$ refers to a redox pair ferrocene/ferrocenium that is used as reference in an electrochemical determination of potential, e.g., cyclovoltammetry.

According to the invention it was furthermore established that in particular the described aryl- and/or heteroaryl-substituted main group element halides and/or pseudohalides can also be used as injection layer in electronic structural parts, preferably between an electrode and a semiconductor layer that can also be doped, or also as blocker layer, preferably between emitter layer and transport layer in electronic structural elements. The compounds used in accordance with the invention have a surprisingly high stability relative to their reactivity with the atmosphere.

Preparation of the aryl- and/or heteroaryl-substituted main group element halides and/or pseudohalides.

The described aryl- and/or heteroaryl-substituted main group element halides and/or pseudohalides can be synthesized according to known processes. The synthesis of such compounds is described, e.g., in the following literature passages, that are included herewith to their full extent as reference in the application. It is understood that the cited literature passages are indicated only by way of example. The preparation of alkyl- and/or heteroalkyl-substituted compounds takes place in an analogous manner. According to O. Glemser et al., e.g., trisaryl compounds of arsenic, phosphorus and antimony can be prepared from the corresponding Grignard compounds and the main group trichlorides, see Angew. Chem. (1964) 76 953; Alonso R. A. et al., JOC (1982) 47(1) 77-80; Fausett B. W. (2005) 70(12) 4851-3. The triaryl compounds obtained in this manner can be oxidized with pure or mixed dihalogen or, e.g., with TeCl4 to dihalogentriaryl compounds, G. S. Harris, A. Kahn, I. Lennon, J. Fluorine Chem. 37 (1987) 247-52; S. N. Bhattacharya, M. Singh, Indian J. Chem. 16A (1978) 778-81; A. Ouchi et al. (1975) 74-99. The halogen groups can be subsequently substituted by other halogen or pseudohalogen groups, A. Otero, P. Royo, J. Organometallic Chem. 154 (1978) 13-9, or by means of aryl or heteroaryl metals such as, e.g., phenyllithium in pentaaryl or -hetaryl compounds, Barton D. H. R. et al., J. Chem. Soc. Chem. Comm. (1980) 17 827-9. Moreover, the triaryl compounds can also be reacted with the corresponding trihalogen compounds to monohalogen or pseudohalogendiaryl or diheteroaryl main group metallic compounds, Bamgboye T. T. C. J. Organometallic Chem. (1989) 362 (1-2) 77-85. Oxygen-bridged aryl main group element compounds are described by M. N. Gibbsons and D. B. Sowerby, phosphorus, sulfur, silicon (1994) 93-4 305-8. Tellurium compounds arylated six times can be produced, e.g., directly from bromine aryls and tellurium tetrachloride in the presence of butyl lithium, see Angew. Chem. Int. Edit. 35(22) 2660-2 (1996): Chem.-A European J. 10(10)2590-2600(2004). The following literature passages can be named as a sample with bridged R groups, JACS 128(21) 6778-9 (2006).

Synthesis of Triaryl and Heteroaryl Antimony Dichlorides

Synthesis of tris(pentafluorophenyl)antimony dichloride

A mixture of 1.5 mmol iodine chloride and 10 ml acetonitrile is slowly added drop by drop to a solution of 1.5 mmol tris(pentafluorophenyl)stilbene in 10 ml acetonitrile under agitation at room temperature. The white crystalline product was obtained from the brown solution after the addition of ether in 65% yield. Fp: 242-4° C.

Synthesis of tris(tetrafluoropyridyl)antimonydichloride

A mixture of 1.5 mmol iodine chloride and 10 ml acetonitrile is slowly added drop by drop to a solution of 1.5 mmol tris(tetrafluoropyridyl)stilbene in 10 ml acetonitrile under agitation at room temperature. The white crystalline product was obtained from the brown solution after the addition of ether in 72% yield. Fp: 242-4°

Doping

Among others, phthalocyanine complexes, e.g., of the Zn (ZnPc), Cu (CuPc), Ni (NiPc) or other metals can be used as p-dopable matrix materials, wherein phthalocyanine ligand can also be substituted. Other metal complexes of naphtocyanines and porphyrines can also be used optionally. Furthermore, arylated or heteroarylated amines or benzidine derivatives can also be used that can be substituted or non-substituted, e.g., TPD, a-NPD, TDATA, especially also spiro-linked ones such as, e.g., spiro-TTB. In particular, a-NPD and spiro-TTD can be used as matrix material.

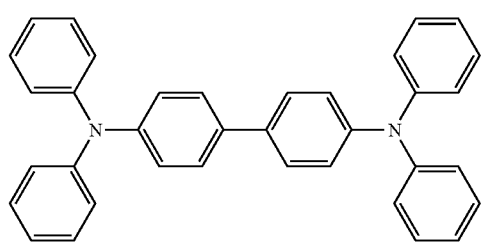

TPD

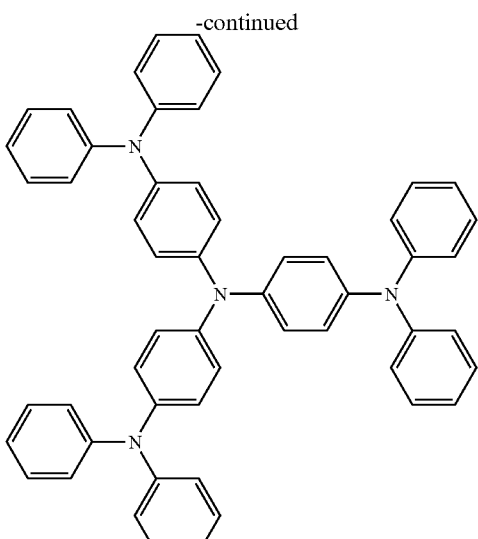

TDATA

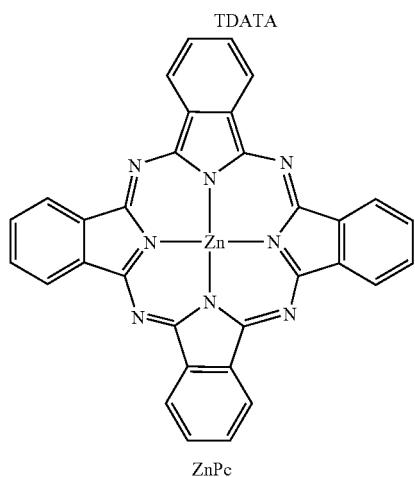

ZnPc

In addition to polyaromatic hydrocarbons, heteroaromatics such as, in particular imidazole, thiazole derivatives, heterotriphenylenes but also others can also be used as matrix material, optionally even dimeric, oligomeric or polymeric heteroaromatics. The heteroaromatics are preferably substituted, especially aryl-substituted, e.g., phenyl-substituted or naphthyl-substituted. They can also be present as spiro compounds.

It is understood that the mentioned matrix materials can also be used mixed with each other or with other materials in the scope of the invention. It is understood that suitable other organic matrix materials that have semiconducting properties can also be used.

Doping Concentration

The dopant is preferably present in a doping concentration of ≤1:1 to the matrix molecule or to the monomeric unit of a polymeric matrix molecule, preferably in a doping concentration of 1:2 or less, especially preferably of 1:5 or less or 1:10 or less. The doping concentration can be in the range of 1:1 to 1:100,000, especially in the range of 1:5 to 10,000 or 1:1.0 to 1,000, e.g., in the range of 1:10 to 1:100 or 1:25 to 1:50 without being limited thereto.

Carrying Out of the Doping

The doping of the particular matrix material with the compounds to be used in accordance with the invention can take place by one or a combination of the following processes:

Mixed evaporation in a vacuum with a source for the matrix materials and one for the dopant.

Sequential depositing of the matrix material and of the p-dopant on a substrate with the subsequent diffusing in of the dopant, in particular by thermal treatment.

Doping of a matrix layer by a solution of p-dopant with subsequent evaporation of the solvent, in particular by thermal treatment.

Surface doping of a matrix material layer by a layer of dopant applied on the surface.

Production of a solution of matrix molecules and dopants and subsequent production of a layer from the solution by conventional methods such as, e.g., evaporation of the solvent or centrifuging it on.

The doping can also optionally take place in such a manner that the dopant is evaporated from a precursor compound that releases the dopant upon being heated and/or irradiated. For example, a carbonyl compound, dinitrogen compound or the like that are split off during the release of the dopant CO, nitrogen or the like can be used as precursor compound with other suitable precursors also being able to be used such as, e.g., salts, e.g., halides or the like. The heat necessary for the evaporation can substantially be made available by an irradiation which can also be irradiated in a targeted manner into certain bands of the compounds and/or precursors or compound complexes such as charge-transfer complexes in order to facilitate the evaporation of the compounds by dissociation of the complexes, e.g., by conversion into excited states. However, the complex can in particular also be sufficiently stable to evaporate in a non-dissociated manner under the given conditions or to be applied onto the substrate. It is understood that other suitable processes can also be used to carry out the doping.

Thus, in this manner p-doped layers of organic semiconductors can be produced that can be used in many different ways.

Semiconducting Layer

Semiconducting layers can be produced by the main group element halides and/or pseudohalides, which layers are optionally preferably designed to be linear such as, e.g., conductivity paths, contacts or the like. The main group element halides and/or pseudohalides can be used here as p-dopants together with another compound that can function as matrix material, wherein the doping ratio can be 1:1 or less. However, the dopant used can also be present in higher amounts relative to the particular compound or component so that the ratio of dopant:compound can be in a ratio >1:1, e.g., in a ratio of ≥2:1, ≥5:1, ≥10:1 or ≥20:1 or higher. The particular other component can be one such as is used as matrix material in the ease of the production of doped layers, without being limited thereto. The dopant use can also be optionally present in pure form, e.g., as pure layer.

The area containing a dopant or consisting substantially or completely of the latter can be contacted in an electrically current-conductive manner with an organic semiconducting material and/or an inorganic semiconducting material, e.g., arranged on such a substrate.

In particular the mentioned electron-poor aryl-substituted and/or heteroaryl-substituted main group element halides and/or pseudohalides are preferably used in accordance with the invention as p-dopants, e.g., in a ratio of ≤1:1 or ≤1:2. Semiconducting layers with conductivities at room temperature in the range of $10^{-5}$ s/cm or higher, e.g., of $10^{-3}$ s/cm or higher, e.g., of $10^{-2}$ s/cm can be achieved by the electron-poor compounds used in accordance with the invention as p-dopants, e.g., when using ZnPe, Spiro-TTB or a-NPD as matrix. When using phthalocyanine zinc as matrix a conductivity of higher than $10^{-8}$ s/cm was achieved. e.g., $10^{-6}$ s/cm. The conductivity of non-doped phthalocyanine zinc on the other hand is maximally $10^{-10}$ s/cm.

It is understood that the layer or the structure with the dopants can contain one or several main group element halides or pseudohalides.

Electronic Structural Element

A plurality of electronic structural elements or equipment containing them with a p-doped organic semiconducting layer earl be produced using the described compounds for producing p-doped organic semiconducting materials that can be arranged in particular in the form of layers or electrical line paths. In the sense of the invention the concept "electronic structural elements" also includes optoelectronic structural elements. The electronic properties of an electronically functionally active area of the structural element such as its electrical conductivity, light-emitting properties or the like can be advantageously changed by the use of the described compounds. Thus, the conductivity of the doped layers can be improved and/or the improvement of the charge carrier injection of contacts into the doped layer can be achieved.

The invention comprises in particular organic light-emitting diodes (OLED), organic solar cells, field-effect transistors, organic diodes, in particular those with a high rectification ratio such as $10^3$-$10^7$, preferably $10^4$-$10^7$ or $10^5$-$10^7$, and field-effect transistors manufactured by the electron-poor aryl-substituted and/or heteroaryl-substituted material elementary halides and/or pseudohalides.

A p-doped layer based on an organic matrix material, e.g., in the following layer structures can be present in the electronic structural element, the base materials or matrix materials of the individual layers preferably being organic:

p-i-n: p-doped semiconductor-intrinsic semiconductor-n-doped semiconductor, n-i-p: n-doped semiconductor-intrinsic semiconductor-p-doped semiconductor.

"i" is a non-doped layer again, "p" is a p-doped layer. The contact materials are hole-injecting here, wherein on the p side, e.g., a layer or a contact of ITO or Au can be provided, or electron-injecting, wherein on the n side a layer or a contact of ITO. Al or Ag can be provided.

In the above structures the i layer can also be omitted if required, as a result of which layer sequences with p-n or n-p transitions can be obtained.

However, the use of the described compounds is not limited to the above-mentioned exemplary embodiments, in particular the layer structures can be supplemented or modified by the introduction of additional suitable layers. In particular, OLEDs with such layer sequences, in particular with pin structure or with a structure inverse to it, can be built up with the described compounds.

In particular, organic diodes of the type metal-insulator-p-doped semiconductor (min) or also, optionally, of the pin type can be produced with the aid of the described p-doping agents, e.g., based on phthalocyanine zinc. These diodes display a rectification ratio of $10^5$ and higher. Furthermore, electronic structural elements with p-n transitions can be produced using the mentioned compounds, wherein the same semiconductor material is used for the p-doped side and the n-doped aside (homo-p-n transition), and wherein a described electron-poor aryl-substituted and/or heteroaryl-substituted main group element halides and/or pseudohalide is used with particular preference for the p-doped semiconductor material.

However, the electron-poor aryl-substituted and/or heteroaryl-substituted main group element halides and/or pseudohalides can also be used in accordance with the invention in the electronic structural elements in layers, conductivity paths, point contacts or the like if the latter predominate relative to another component, e.g. as injection layer in pure or in the substantially pure form.

Further tasks and advantages of the present invention will now be described in an illustrating manner using the following examples that are to be considered as only illustrative and not as limiting the scope of the invention.

EXAMPLES OF APPLICATION

An extremely electron-poor aryl-substituted and/or heteroaryl-substituted main group element halide or pseudohalide is provided in a very clean manner.

The presented electron-poor aryl-substituted and/or heteroaryl-substituted main group element halide or pseudohalide is evaporated at the same time with the matrix material. According to the exemplary embodiment the matrix material is phthalocyanine zinc, spiro-TTB or a-NDP. The p-dopant and the matrix material can be evaporated in such a manner that the layer precipitated on a substrate in a vacuum evaporation system has a doping ratio of p-dopant to matrix material of 1:10.

The layer of the organic semiconducting material doped with the p-dopant is applied on an ITO layer (indium tin oxide) arranged on a glass substrate. After application of the p-doped organic semiconducting layer a metal cathode is applied, e.g., by evaporation of a suitable metal, in order to produce an organic light-emitting diode. It is understood that the organic light-emitting diode can also have a so-called inverted layer design, wherein the layer sequence is: glass substrate-metal cathode-p-doped organic layer-transparent conductive cover layer (e.g., ITO). It is understood that further layers can be provided between the individual mentioned layers, depending on the application.

Example 1

Tris(pentafluorophenyl)antimony dichloride

The neutral antimony compound was used for the doping of ZnPc as matrix material. Doped layers with a doping ratio of doping agent:matrix material of 1:10 were produced by mixed evaporation of matrix and doping agent with ZnPc. The conductivity was $3\times10^{-4}$ S/cm.

Example 2

Tris(pentafluorophenyl)antimony dichloride

The neutral antimony compound was used for the doping of spiro-TTB as matrix material. Doped layers with a doping ratio of doping agent:matrix material of 1:10 were produced by mixed evaporation of matrix and doping agent with spiro-TTB. The conductivity was $3\times10^{-7}$ S/cm.

Example 3

Tris(tetrafluoropyridyl)antimony dichloride

The neutral antimony compound was used for the doping of ZnPc as matrix material. Doped layers with a doping ratio of doping agent matrix material of 1:10 were produced by mixed evaporation of matrix and doping agent with ZnPc. The conductivity was $3.1\times10^{-4}$ S/cm.

Example 4

Tris(tetrafluoropyridyl)antimony dichloride

The neutral antimony compound was used for the doping of spiro-TTB as matrix material. Doped layers with a doping ratio of doping agent:matrix material of 1:10 were produced by mixed evaporation of matrix and doping agent with spiro-TTB. The conductivity was $1.8 \times 10^{-7}$ S/cm.

The features of the invention disclosed in the previous description and in the claims can be essential for the realization of the invention in its different embodiments both individually as well as in any combination.

The invention claimed is:

1. An organic semiconducting material comprising at least one organic matrix compound and one dopant, wherein the dopant is a p-dopant having lias the following structure:

$$R_{1-6}\text{-M-}X_{0-5},$$

wherein M is selected from S, Se, or Te; or $$R_{1-5}\text{-M-}X_{0-4},$$

wherein M is selected from P, As, Sb, or Bi;
wherein each R is independently selected from the group consisting of substituted or non-substituted aryl or substituted or non-substituted heteroaryl;
wherein X is independently selected from halogen or pseudohalogen;
wherein the sum of the two subscripts representing the number of R and X substituents is (i) equal to 6 if M is selected from S, Se, or Te, or (ii) equal to 5 if M is selected from P, As, Sb, or Bi; and
wherein any of groups R may be connected to each other at least in pairs, directly or via a bridge.

2. The organic semiconducting material according to claim 1, wherein a molar doping ratio of the dopant to a matrix molecule of the at least one organic matrix compound is between 20:1 and 1:100,000, wherein when the at least one organic matrix compound is a polymer, the matrix molecule is a monomeric unit of the polymer.

3. An electronic or optoelectronic structural element comprising at least one main group element halide and/or pseudohalide as a p-dopant for doping an organic semiconducting matrix material, a charge injection layer, a hole blocker layer, an electrode material, a transport material, or a memory material, wherein the main group element halide and/or pseudohalide has the following structure:

$$R_{1-6}\text{-M-}X_{0-5},$$

wherein M is selected from S, Se, or Te; or $$R_{1-5}\text{-M-}X_{0-4},$$

wherein M is selected from P, As, Sb, or Bi;
wherein each R is independently selected from the group consisting of substituted or non-substituted aryl or substituted or non-substituted heteroaryl;
wherein X is independently selected from halogen or pseudohalogen;
wherein the sum of the two subscripts representing the number of R and X substituents is (i) equal to 6 if M is selected from S, Se, or Te, or (ii) equal to 5 if M is selected from P, As, Sb, or Bi; and
wherein any of groups R may be connected to each other at least in pairs, directly or via a bridge.

4. The electronic or optoelectronic structural element according to claim 3, wherein one or more of the substituted or non-substituted aryl or substituted or non-substituted heteroaryl substituents is substituted independently with halogen and/or acceptor substituents.

5. The electronic or optoelectronic structural element according to claim 3, wherein the halide and/or pseudohalide further comprises at least one neutral co-ligand.

6. The electronic or optoelectronic structural element according to claim 3, wherein X is selected from CN, OCN, SCN, or $N_3$.

7. The electronic or optoelectronic structural element according to claim 3, wherein X is Cl.

8. The electronic or optoelectronic structural element according to claim 3, comprising an electronically functional active area, wherein the active area comprises the main group element halide and/or pseudohalide.

9. The electronic or optoelectronic structural element according to claim 8, wherein the electronically active area comprises an organic semiconducting matrix material that is doped with the at least one p-dopant for changing the electronic properties of the semiconducting matrix material.

10. The electronic or optoelectronic structural element according to claim 3, wherein the element is in the form of an organic light-emitting diode, a photovoltaic cell, an organic solar cell, an organic diode, an organic field-effect transistor or a photo-initiated or magnetic memory.

* * * * *